(12) United States Patent
Lee et al.

(10) Patent No.: US 7,399,486 B2
(45) Date of Patent: Jul. 15, 2008

(54) METHOD OF PREPARING MIXED FORMULATION OF SUSTAINED RELEASE MICROSPHERES BY CONTINUOUS ONE-STEP PROCESS

(75) Inventors: Hee Yong Lee, Daejeon (KR); Sung Kyu Kim, Daejeon (KR); Jung Soo Kim, Daejeon (KR); Ji Suk Lee, Daejeon (KR); Young Hwan Jung, Daejeon (KR); Jung In Kim, Daejeon (KR); Yun Mi Seo, Cheonan-si (KR); Ho-Il Choi, Daejeon (KR); Seung Gu Chang, Daejeon (KR); Kee Don Park, Daejeon (KR)

(73) Assignee: Peptron Co., Ltd. (KR)

( * ) Notice: Subject to any disclaimer, the term of this patent is extended or adjusted under 35 U.S.C. 154(b) by 183 days.

(21) Appl. No.: 10/562,379

(22) PCT Filed: Jun. 25, 2004

(86) PCT No.: PCT/KR2004/001558

§ 371 (c)(1),
(2), (4) Date: Jul. 10, 2006

(87) PCT Pub. No.: WO2004/112752

PCT Pub. Date: Dec. 29, 2004

(65) Prior Publication Data

US 2007/0059363 A1 Mar. 15, 2007

(30) Foreign Application Priority Data

Jun. 26, 2003 (KR) .................. 10-2003-0042249

(51) Int. Cl.
*A61K 9/22* (2006.01)

(52) U.S. Cl. .................................................... 424/468
(58) Field of Classification Search ................ 424/460, 424/468, 469, 489–502; 427/212–214; 428/402.21, 428/403, 407; 514/12
See application file for complete search history.

(56) References Cited

U.S. PATENT DOCUMENTS 4,360,598 A * 11/1982 Otagiri et al. ............... 501/103
4,554,887 A * 11/1985 Yoakam et al. ............. 118/666

(Continued)

*Primary Examiner*—Sharon E. Kennedy
*Assistant Examiner*—Suezu Ellis
(74) *Attorney, Agent, or Firm*—Casimir Jones, S.C.

(57) ABSTRACT

Disclosed is a method for preparing a mixed formulation of sustained release microspheres with various compositions by a continuous one-step process. The present method is characterized by preparing the mixed formulation of sustained release microspheres with different compositions by a continuous one-step process by continuously introducing the mixed fluids into a dryer from the two or more different fluids for preparation of sustained release microspheres containing a biodegradable polymer, a drug, an additive and a solvent with different types of contents or both of the components, by controlling the mixing ratios of the fluids according to the time, unlike a conventional method including spray-drying a mixture of microspheres containing a biodegradable polymer, a drug, an additive and a solvent with a single composition. The present method can achieve a desired drug release, which is difficult to be obtained by conventional microspheres with a single composition, by preparing microspheres by a continuous one-step process, and can simplify the conventional complex process of separately preparing several microsphere formulations and then mixing the formulations at a proper ratio to achieve a desired drug release.

9 Claims, 6 Drawing Sheets

U.S. PATENT DOCUMENTS

| | | | |
|---|---|---|---|
| 4,777,033 A * | 10/1988 | Ikura et al. | 424/44 |
| 4,798,694 A * | 1/1989 | Sugata et al. | 264/651 |
| 5,489,439 A * | 2/1996 | Bola | 424/489 |
| 5,723,269 A * | 3/1998 | Akagi et al. | 424/497 |
| 6,451,349 B1 * | 9/2002 | Robinson et al. | 424/489 |
| 2004/0240311 A1 * | 12/2004 | Hashiba | 366/101 |

* cited by examiner

METHOD OF PREPARING MIXED FORMULATION OF SUSTAINED RELEASE MICROSPHERES BY CONTINUOUS ONE-STEP PROCESS

BACKGROUND OF THE INVENTION

1. Field of the Invention

The present invention relates to a method of preparing a mixed formulation of sustained release microspheres with different compositions by a continuous one-step process.

2. Description of the Prior Art

Sustained release of drugs at constant rates is conventionally achieved by preparing microspheres with a single composition using a single mixture of a biodegradable polymer, a drug, an additive, a solvent, and the like, by a spray-drying method or other methods. From the sustained release microspheres, the release of a drug must be properly controlled at the initial phase and for a continuous period to obtain optimal pharmaceutical efficacy for a predetermined period of time. To date, the initial release and continuous release of a drug have been controlled by employing microspheres prepared by varying the following parameters: type and concentration of the biodegradable polymer, content of the drug, amount of the additive for control of the release rate of the drug, solvent type, and the like. Other parameters also can control the drug release by changing several physical properties of the microspheres, which include, in case of using a spray-drying method, solution spraying method, spray nozzle type, feeding rate of a solution to be sprayed, amount of air supplied to a spray nozzle for an air-assisted atomization, frequency of ultrasonic wave for an ultrasonic atomization, supplied amount of drying air, supply rate and temperature of the drying air and the like.

Of the above parameters, the biodegradable polymer type is the most important factor determining the release rate of drugs from microspheres. Among several biodegradable polymers used in the preparation of sustained release microspheres, the most widely used one is poly(lactide-co-glycolide) (PLGA) (DeLuca, P. P. et al., Biodegradable polyesters for drug and polypeptide delivery, in: El-Nokaly, M. A., Piatt, D. M., and Charpentier, B. A. (Eds.), Polymeric delivery systems, properties and applications, American Chemical Society, pp. 53-79 (1993); Park, T. G., *Biomaterials*, 16, 1123-1130 (1995); Anderson, J. M. and Shive, M. S., *Adv. Drug. Del. Rev.*, 28, 5-24 (1997); Tracy, M. A. et al., *Biomaterials*, 20, 1057-1062 (1999)). PLGA has characteristic physicochemical features in that, for example, its biodegradation rate varies according to the ratio of lactic acid residues to glycolic acid residues, and their molecular weights and hydrophilicity, and, thus, PLGA is a major factor to determine durations of drug release. Therefore, when a drug delivery system for sustained release of a drug for a predetermined period is prepared, one must first select a polymer being properly biodegraded for the predetermined period. In particular, when drug release is desired to be maintained for a period longer than one month, sustained release microspheres are prepared by employing PLGA copolymers with higher lactic acid content, higher molecular weights, or lower hydrophilicity. However, there is a significant problem with the sustained release microspheres prepared using only a single polymer selected as described above, as follows. Since the polymer is degraded at very slow rates, a drug encapsulated in the microspheres is often not released at the initial phase. Also, this problem cannot be overcome by varying the aforementioned parameters, thereby making it difficult to obtain desired release patterns of drugs for a desired long period.

On the other hand, many recent studies are associated with an alternative method of preparing microspheres for sustained release of drugs, which includes mixing two or more polymers with different degradation rates at a predetermined ratio to control both initial release and continuous release of the drugs from the microspheres (Ravivarapu, H. B., Burton, K., DeLuca, P. P., Polymer and microsphere blending to alter the release of a peptide from PLGA microspheres, *Eur J Pharm Biopharm*, 50(2), 263-70, 2000). However, the microsphere formulation comprising a blend made from two or more different polymers with a single composition is also problematic in that, in a single microsphere, a rapidly degraded polymer affects the degradation rate of other polymers having relatively slow degradation rates, resulting in an increase in degradation of the microsphere. Thus, the microsphere formulation prepared by combining two or more polymers at a single (fixed) ratio is not effective in achieving both desired initial release and continuous release of drugs for a long period.

The disadvantage of the single-composition microsphere formulation can be overcome by separately preparing two or more microsphere formulations using two or more different polymers and combining the microsphere formulations at a proper ratio to give a microsphere formulation allowing for sustained release of drugs for a desired period (U.S. Pat. No. 4,897,268, Burton, K. W., Shameem, M., Thanoo, B. C., DeLuca, P. P., Extended release peptide delivery systems through the use of PLGA microsphere combinations, *J Biomater Sci Polym Ed.* 11(7), 715-29, 2000, Ravivarapu, H. B., Burton, K., DeLuca, P. P., Polymer and microsphere blending to alter the release of a peptide from PLGA microspheres, *Eur J Pharm Biopharm*, 50(2), 263-70, 2000). However, this microencapsulation is a complicated and uneconomical process because two or more kinds of microspheres should be individually prepared to achieve desired drug release patterns.

Therefore, with respect to the preparation of sustained release microspheres encapsulating drugs, there is a need for a simple and economical method that is capable of achieving a desired release of drugs regardless of a desired period.

SUMMARY OF THE INVENTION

The present invention aims to provide a method of preparing microspheres capable of easily achieving a desired release of drugs by preparing a mixed formulation of microspheres with multiple compositions by a continuous one-step process, unlike the conventional complex, ineffective method including separately preparing two or more microsphere formulations and mixing the formulations to overcome the excessive initial drug release or sharply reduced or increased drug release with the passage of time.

Leading to the present invention, the intensive and thorough research into the preparation of microspheres by a continuous one-step process including continuously introducing mixed fluids into a dryer from two or more different fluids for preparation of sustained release microspheres containing a biodegradable polymer, a drug, an additive and a solvent with different types or contents or both of the components, by controlling the mixing ratios of the fluids according to the time, conducted by the present inventors, resulted in the finding that a mixed formulation of microspheres varying in the drug content, the biodegradable polymers composition, and the like can easily control the release of the drug from the microspheres.

The present invention provides a method of preparing a mixed formulation of sustained release microspheres with different compositions, including preparing two or more different fluids for preparation of the sustained release microspheres containing a biodegradable polymer, a drug, an additive and a solvent with different types or contents or both of one or more of the components, and continuously supplying the mixed fluids from two or more different fluids to a dryer via a single spray nozzle by controlling the mixing ratios of the fluids according to the time to dry the fluids.

Preferably, in the step of consecutively supplying the two or more different fluids to the dryer, the fluids are mixed by controlling the mixing ratios of the fluids using a gradient pump.

Also, the fluids supplied to the dryer are preferably dried by a spray-drying method, a spray freeze-drying method, or a supercritical fluid-based drying method. In particular, the spray-drying method is preferable.

The method may further include dispersing the sustained release microspheres in a solution containing a dispersion excipient and freeze-drying a resulting solution. In the method, the biodegradable polymer is preferably one or more selected from the group consisting of polylactide, polyglycolide, poly(lactide-co-glycolide), polyorthoesters, polyanhydrides, polyamino acids, polyhydroxybutyric acid, polycaprolactone, polyalkylcarbonate, lipids, fatty acids, waxes, and derivatives and mixtures thereof, particularly preferably, selected from polylactide and poly(lactide-co-glycolide).

In addition, the drug used in the present method is preferably selected from among peptides and proteins, more preferably, peptides of 2 to 60 amino acid residues in length, and particularly preferably, luteinizing hormone releasing hormone (LHRH) analogs, octreotide and salts thereof

BRIEF DESCRIPTION OF THE DRAWINGS

The above and other objects, features and other advantages of the present invention will be more clearly understood from the following detailed description taken in conjunction with the accompanying drawings, in which:

FIGS. 1a to 1c illustrate an aspect of preparing microspheres with multiple compositions by a continuous one-step process according to the present invention, wherein

DETAILED DESCRIPTION OF THE INVENTION

The present invention relates to a method of preparing a mixed formulation of sustained release microspheres with different compositions by a continuous one-step process, including continuously supplying the mixed fluids from two or more different fluids for preparation of the sustained release microspheres to a dryer by controlling the mixing ratios of the fluids according to the time to dry the fluids.

In an aspect, the present invention relates to a method of preparing a mixed formulation of sustained release microspheres with different compositions by a continuous one-step process, including preparing two or more different fluids for preparation of the sustained release microspheres containing a biodegradable polymer, a drug, an additive and a solvent with different types or contents or both of one or more of the components, and continuously supplying the mixed fluids from the two or more different fluids to a dryer by controlling the mixing ratios of the fluids according to the time to dry the fluids.

The term "biodegradable polymer", as used herein, includes polylactide (PLA), polyglycolide (PGA) or their copolymer, poly(lactide-co-glycolide) (PLGA), polyorthoesters, polyanhydrides, polyamino acids, polyhydroxybutyric acid, polycaprolactone, polyalkylcarbonate, lipids, fatty acids, waxes, and derivatives and mixtures thereof.

The above examples of the biodegradable polymer are provided only to illustrate the present invention, and the present invention is not limited to them.

In particular, among the aforementioned biodegradable polymers, the polyesters, such as PLA, PGA or PLGA, are approved to be biocompatible and safe to the body because they are metabolized in vivo to harmless lactic acid and glycolic acid by hydrolysis. The degradation of the polyesters may be controlled at various rates according to the molecular weight, the ratio of the two monomers, the hydrophilicity, and the like, for various durations ranging from a short period of one to two weeks to a long period of one to two years. The polyesters are polymeric substances that have been approved for use in humans in several tens of countries, including by the U.S. Food and Drug Administration (FDA), and commercialized. Therefore, the polyesters may be preferably used in the present invention. In particular, the polyesters such as PLGA or PLA are preferably used in the present invention.

The drug applicable in the present invention includes all drugs in various forms, such as peptides, proteins and synthetic organic compounds. The drugs may have various biological activities, for example, serving as anticancer agents, antibiotics, analgesics, antiinflammatory agents, sedatives, antiulcer agents, antidepressants, antiallergenic agents, therapeutic agents for treatment of diabetes mellitus, therapeutic agents for treatment of hyperlipidemia, antituberculous agents, hormonal agents, anesthetics, bone metabolic agents, immunomodulators, angiogenesis modulators, contraceptives, and vitamin-like agents, but are not limited to them.

Biologically active peptide and protein drugs are preferably used in the present invention. Especially preferred biologically active peptides are biologically active peptides of 2 to 60 amino acid residues, salts thereof or analogues thereof. Examples of peptides composed of 5 or fewer amino acid residues in length include glutathione, homoglutathione, endomorphin, thymopoietin and enkephalin. Examples of peptides composed of 10 or fewer amino acid residues include growth hormone release peptide-2 and -6 (GHRP-2 and -6), octreotide, carbetocin, oxytocin, cholecystokinin, vasopressin, bradykinin, delta sleep-inducing peptide, angiotensin I, II and III, neurokinin A and B, neuromedin B, triptorelin, leuprolide, goserelin, nafarelin, buserelin, histerelin, antide, argtide, orntide, and cetrorelix. Examples of peptides composed of 20 or fewer amino acid residues include hirudin, alloferin 1 and 2, IGF-1 analogues, cortistain-17, dynorphin A and B, α-endorphin, γ-endorphin, gastrin, guanylin, uroguanylin, and substance P. Examples of peptides composed of 30 or fewer amino acids include defensin 1 and 2, gastrin releasing peptide, secretin, endothelin, and glucagon-like peptide-2. Examples of peptides composed of 40 or fewer amino acid residues include ceropin A, B and P1, pancreatic polypeptide, amylin, calcitonin, calcitonin gene related peptide (37 amino acids), β-endorphin (37 amino acids), and Big endothelin-1. Examples of peptides composed of 60 or fewer amino acid residues include corticotropin releasing factor, growth hormone releasing factor (GRF), adrenomedullin, C-type natriuretic peptide, and insulin. More preferred are biologically active peptides of 3 to 30 amino acid residues in length, and most preferred are biologically active peptides of 5 to 20 amino acid residues in length.

In particular, peptide drugs such as luteinizing hormone releasing hormone (LHRH) analogs or octreotide may be preferably used in the present invention.

The LHRH analogues refer to peptides that, when administered to the body, inhibit the secretion of LH by the pituitary gland (in case of LHRH agonists, the secretion of LH is stimulated in the early phase but is inhibited upon continuous release), leading to inhibition of secretion of testosterone and estrogen, and that, due to this action, have therapeutic efficacy on hormone-dependent diseases, such as prostatic cancer, endometriosis and uterine myoma. Non-limiting examples of the LHRH analogs include LHRH agonists, such as triptorelin, leuprolide, goserelin, nafarelin, buserelin, histerelin and salts thereof, and LHRH antagonists, such as antide, argtide, orntide, cetrorelix and salts thereof.

Octreotide, which is a somatostatin variant, is a peptide drug consisting of eight amino acids. Octreotide has stronger affinity to somatostatin receptors than the naturally occurring somatostatin, and, thus, is more effective in inhibiting the release of growth hormone, glucagons and insulin than somatostatin. In addition, octreotide suppresses the release of luteinizing hormone (LH) by gonadotropin-releasing hormone, decreases splanchnic blood flow, and inhibits the release of serotonin, gastrin, vasoactive intestinal peptide (VIP), secretin, motilin, and the like. By virtue of these pharmacologic actions, octreotide has been used to treat the symptoms associated with metastatic carcinoid tumors (flushing and diarrhea) and vasoactive intestinal peptide (VIP)-secreting adenomas (watery diarrhea). Also, octreotide has been used to reduce the release of growth hormone and insulin-like growth hormone in acromegaly patients.

The term "fluid for preparation of sustained release microspheres", as used herein, refers to a fluid that is a mixture of a biodegradable polymer, a drug, an additive, a solvent, etc., which are used for preparation of the sustained release microspheres, and includes a suspension, an emulsion and a solution. The preferred fluid is a solution.

Preferably, according to the present method, a mixed formulation of sustained release microspheres is prepared by a continuous one-step process by preparing two or more different suspensions, emulsions or solutions containing different types or contents or both of a biodegradable polymer and/or a drug, and supplying the mixed fluids from two or more different fluids to a dryer via a gradient pump by controlling the mixing ratios of the fluids. In detail, according to the present invention, a mixed formulation of sustained release microspheres with different compositions is prepared by a continuous one-step process by suspending or emulsifying a drug to be encapsulated at same or different concentrations in solutions of biodegradable polymers of different types or solutions of an identical biodegradable polymer of different concentrations, more preferably, dissolving the drug in the polymer solution, and supplying the resulting solutions to a dryer via a gradient pump by controlling the mixing ratios of the fluids according to the time.

The release pattern of a drug from sustained release microspheres greatly depends on hydration rate and degradation rate of a polymer used, affinity of the drug to the polymer, surface or internal morphology of the microspheres, and the like. The hydration and degradation rates of the polymer depend on hydrophilicity thereof. In case of PLGA or PLA polymers, polymers having free carboxyl end groups (e.g., RG502H, RG503H, RG504H, R202H, R203H, etc., which are produced by Boehinger Ingelheim) are more rapidly hydrated due to their high hydrophilicity than polymers having carboxyl end groups substituted with alkyl groups such as dodecyl groups (e.g., RG502, RG503, RG504, R202, R203, etc., which are produced by Boehinger Ingelheim), and, thus, are rapidly degraded in vivo. In addition, the degradation rate of the polymer greatly depends on the molecular weight and the ratio of the lactic acid residues to the glycolic acid residues. PLGA polymers including lactic acid residues and glycolic acid residues at a ratio of 50:50 are most quickly degraded, which are exemplified by RG502H, RG502 and RG503H, and, among the PLGA polymers containing lactic acid residues to glycolic acid residues at an equal content, low molecular weight polymers are more quickly degraded. As polymers have higher lactide contents, such as RG7525(H) or RG8515(H), they are degraded at slower rates. Thus, among polymers with an identical molecular weight, PLA polymers consisting of only lactic acids, such as R202(H) or R203(H), are most slowly degraded. With regard to the degradation rate of the polymer and other factors, PLGA polymers including lactic acid residues and glycolic acids at a ratio of 50:50 are used when drugs are desired to be released within one month. Polymers including 75% or 100% lactic acid residues are used mainly when drugs are desired to be released for two to three months or for a longer period of time.

The additive applicable in the fluid for the preparation of sustained release microspheres of the present invention may include sucrose, trehalose, maltose, mannitol, lactose, mannose, cyclodextrin, dextran, polyethylene glycol, polyvinylpyrrolidone, albumin, surfactants, amino acids, lactic acid, and inorganic salts. The solvent applicable in the fluid for the preparation of sustained release microspheres of the present invention may include glacial acetic acid, formic acid, acetonitrile, ethylacetate, acetone, methylethylketone, methylene chloride, chloroform, ethanol, and methanol.

In the present method, two or more different fluids for the preparation of sustained release microspheres may be dried by a spray-drying method, a spray freeze-drying method, or a supercritical fluid-based drying method. Preferred is the spray-drying method. The phase separation, solvent extraction and evaporation methods, which are conventionally used to prepare microspheres, have problems in that it is difficult to prepare microphseres with high contents of drugs due to nature of the drugs, or several processing parameters including viscosity, temperature and ratios of solutions used and methods of mixing the solutions should be finely controlled. The problems with the conventional methods further include that toxic solvents are generally used in large amounts, and that drug-loaded microspheres are prepared by a complicated process, resulting in the difficulty in mass production of the micospheres. By contrast, the spray drying process is a beneficial way of preparing microspheres by spraying a solution via a spray nozzle and instantaneously drying the sprayed solution using dry air. The spray drying method is advantageous in terms of facilitating the preparation of microspheres 
containing high contents of drugs regardless of nature of the drugs, and providing a simple process allowing mass production of the microspheres.

When microspheres are prepared by the spray-drying method, the release rate of a drug, as described above, greatly depends on the compositions of solutions to be sprayed, such as composition or content of a biodegradable polymer, drug content, additive type or content and solvent amount. In addition to the above processing parameters, other parameters affecting the size or morphology of microspheres may be employed to control the release rate of drugs, which include methods of spraying the solutions (for example, spraying methods using pressure, air and ultrasonic wave), spray nozzle type, feeding rate of solutions to be sprayed, size of sprayed droplets (for example, in case of using the air spraying method using air, amount of air supplied to the spray nozzle; in case of using the ultrasonic spraying method, frequency of ultrasonic wave), supplied amount of drying air, and supply rate and temperature of the drying air.

Since the present invention aims to prepare a microsphere formulation capable of controlling the release rate of drugs by employing two or more spray solutions with different compositions, it will be apparent to those skilled in the art that other parameters excepting the composition and supply method of the spray solutions are properly controlled according to the purpose of the present invention.

Figure 1A:
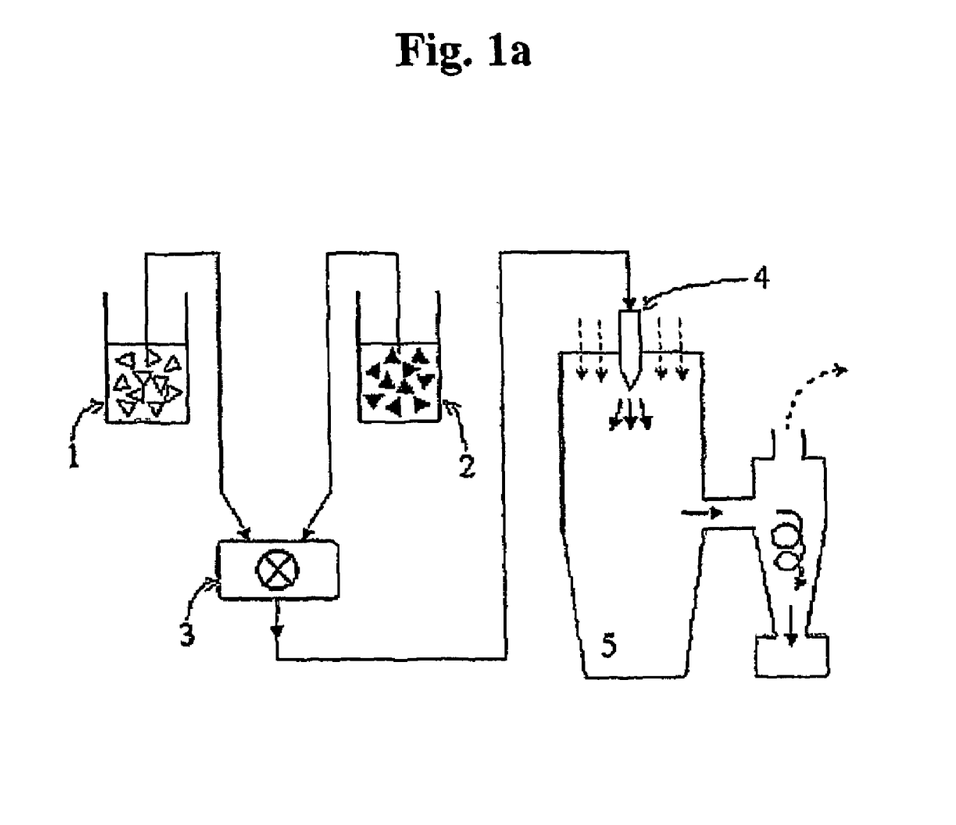
FIG. 1a shows a series of constituents of an apparatus used in preparing the microspheres according to the present invention.
Figure 1B:
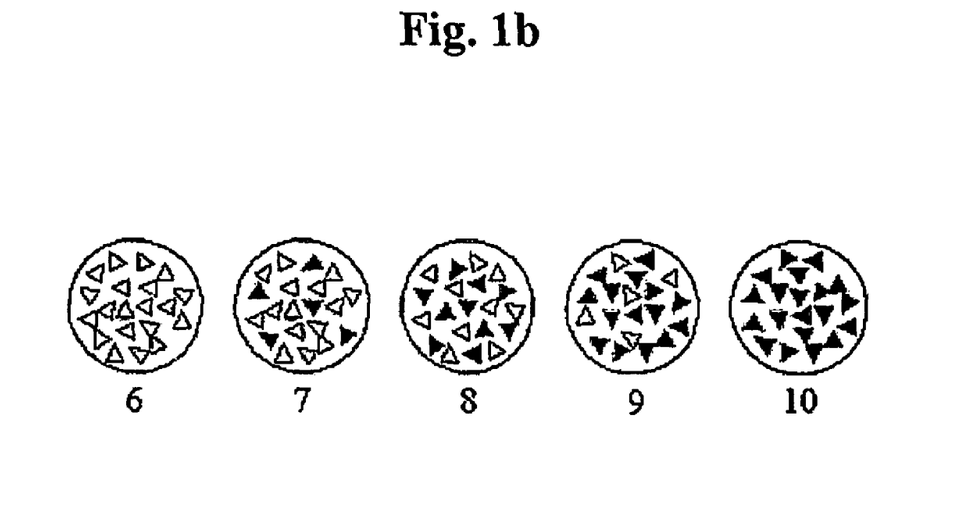
FIG. 1b shows resulting microspheres with different compositions, which are prepared by supplying fluids to be sprayed to a spray nozzle by controlling the mixing ratios of the fluids according to the time.
Figure 1C:
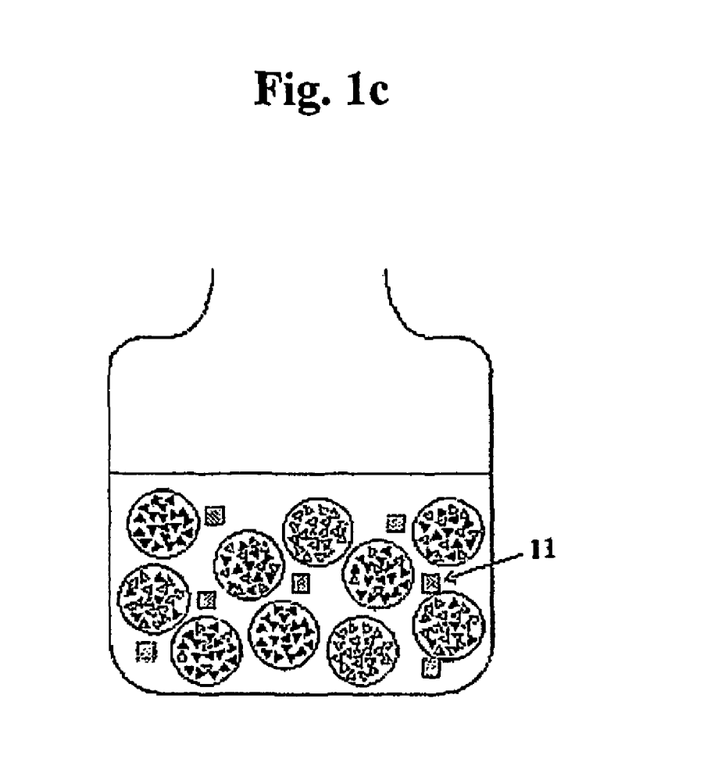
FIG. 1c shows a mixed formulation of the microspheres with various compositions, which is a final product obtained by a process following a spray-drying process.

FIGS. 1a to 1c illustrate an aspect of the method of preparing microspheres with multiple compositions by a continuous one-step process according to the present invention. Based on the aspect, the present invention will be described in more detail below. FIG. 1a shows a series of constituents of an apparatus used in preparing the microspheres according to the present invention. FIG. 1b shows resulting microspheres with different compositions, which are prepared by supplying fluids to be sprayed to a spray nozzle by controlling the mixing ratios of the fluids according to the time. FIG. 1c shows a mixed formulation of the microspheres with various compositions, which is a product obtained by a process following a spray-drying process, for example, a process including dispersing the microspheres in a solution containing a dispersion excipient and freeze-drying a resulting solution.

As shown in FIG. 1a, two or more solutions (1 and 2) to be sprayed according to the present invention are prepared, which individually contains a biodegradable polymer, a drug, an additive and a solvent with different types of one or more of the components. In each solution, the drug or the additive may be present in a suspended or emulsified form, and more preferably, in a completely dissolved form, in a solution in which the biodegradable polymer is dissolved.

The solutions are prepared with different compositions according to the intended use of sustained release microspheres to be prepared. For example, when the initial release of a drug is to be properly controlled, the drug is used in different amounts, or an additive affecting the initial release of the drug is used in different amounts. When the release of a drug is to be controlled for a relatively long period, polymers with different biodegradation rates are employed, or an additive influencing the degradation of a biodegradable polymer is used in different amounts, or different types thereof are used. Most preferably, the composition of each of the solutions is determined based on release profiles for a single-composition microsphere formulation prepared by a spray-drying method commonly used in the art.

The two or more solutions with different compositions, prepared according to the above method, may be supplied to a dryer by controlling the mixing ratios of the fluids according to the time using a pump. The two or more solutions with different compositions may be mixed manually or automatically at a predetermined ratio. As described above, FIGS. 1a to 1c illustrate one aspect of the present invention, in which two or more solutions with different compositions are automatically mixed by a gradient pump equipped with a controller. As shown in FIG. 1a, the mixed fluids from two solutions are supplied to a spray dryer by controlling the mixing ratios of the fluids according to the time by the gradient pump 3. The solutions may be mixed under the control of the controller in various forms of gradients, for example, a linear gradient, a radial gradient or a step gradient. The gradient pump 3 may be one commonly used in liquid chromatography. For example, using a 4-solvent gradient pump, four spray solutions with different compositions are also supplied to a spray nozzle at individually different ratios. The solutions mixed at different ratios according to the time by the gradient pump are introduced into a spray dryer 5 via a spray nozzle 4, and then dried by drying air according to a conventional method of preparing microspheres using a spray dryer.

In addition to upon the preparation of sustained release microspheres using a spray dryer, the method of providing spray solutions using a gradient pump by controlling the mixing ratios of the fluids according to the time may be applicable upon preparation of microspheres by removing a solvent after solution atomization, for example, a spray freeze drying process (U.S. Pat. Nos. 5,019,400 and 5,654,010; Cleland, J. L. et al., Emerging protein delivery methods, *Current Opinion in Biotechnology*, 12, 212-210, 2001), and a supercritical fluid-based process (U.S. Pat. No. 5,043,280; Breitenbach, A., Mohr, D., Kissel, T., Biodegradable semi-crystalline comb polyesters influence the microsphere production by means of a supercritical fluid extraction technique (ASES), *J Control Release*, 63(1-2), 53-68, 2000; Cheng, Y. S. et al., Particle characteristics and lung deposition patterns in a human airway replica of a dry powder formulation of polylactic acid produced using supercritical fluid technology, *J Aerosol Med.,* 16(1), 65-73, 2003).

When microspheres, as prepared above by mixing the spray solutions by controlling the mixing ratios of the fluids according to the time, are collected at regular intervals of the time, as shown in FIG. 1*b*, microsphere collections 6 to 10 were found to have different compositions. The microsphere collections 6 to 10 have different drug release patterns according to the nature of their components. The microsphere collections 6 to 10 shown in FIG. 1*b* were obtained according to the time when the two solutions 1 and 2 of FIG. 1*a* were mixed in a linear gradient from 100% solution 1 to 100% solution 2. After a drying process, the microsphere collections 6 to 10 with different compositions according to the time may be, for example, dispersed in a solution containing a dispersion excipient 11, such as mannitol or carboxymethylcellulose, and subjected to a freeze-drying process to produce a final mixed formulation of microspheres with various compositions (FIG. 1*c*).

A better understanding of the present invention may be obtained through the following examples which are set forth to illustrate, but are not to be construed as the limit of the present invention.

EXAMPLE

Two solutions were mixed and supplied to a spray dryer using an Econo Gradient Pump (Bio-Rad), and microspheres were prepared using an experimental spray dryer, Buchi-191. When glacial acetic acid was used as a solvent, drying air at 65° C. to 95° C. was supplied. When methylene chloride was used as a solvent, drying air at 50° C. was supplied. Compressed air for solution atomization was supplied in an amount of 300 to 500 Nl/h. Solution feed rate, drying air amount and other parameters varied depending on each experiment. Prepared microspheres were dispersed in aqueous mannitol solution, and then freeze-dried. In vitro release tests for formulations containing leuprolide or octreotide were carried out using 5 mg/ml of microspheres in 10 mM PBS (pH 7.4) at 37° C. The peptide-loaded microspheres in PBS buffer were incubated at 37° C. and aliquots were taken at various time points. After centrifugation of the aliquots, the released peptides in the supernatants were analyzed by reverse-phase high performance liquid chromatography using an UV detector (220 nm or 280 nm) or a fluorescence detector (Ex: 280 nm; Em: 350 nm).

Microspheres, prepared in the following Preparational Example and Comparative Preparational Examples by mixing at proper ratios solutions with an identical drug content but different types of polymers using a gradient pump and spray-drying the mixture, were found to have various drug release patterns.

Preparational Example 1

Preparation of Mixed Formulations of Leuprolide-loaded Microspheres with a Different Type of Polymers Leuprolide was added to each of RG502H, RG503H and R202H polymers in an amount of 12 wt %, and glacial acetic acid was added to the mixture in an amount allowing a final polymer concentration of 5% (w/w), followed by homogeneous mixing, thus giving three solutions. Two of the three solutions were supplied to a spray dryer using a gradient pump at a total flow rate of 2.4 ml/min, thus yielding leuprolide-loaded microspheres with various polymer compositions. The ratio of the solutions according to the time for each formulation is given in Table 1, below.

TABLE 1

| | | Total flow rate (2.4 ml/min) | | |
| --- | --- | --- | --- | --- |
| | Solutions | 0-3 min | 3-6 min | 6-9 min |
| Formulation 1 | RG502H | 33% | 33% | 33% |
| | RG503H | 67% | 67% | 67% |
| Formulation 2 | RG502H | 0 → 20% | 20 → 40% | 40% |
| | RG503H | 100 → 80% | 80 → 60% | 60% |
| Formulation 3 | RG502H | 40 → 30% | 30 → 0% | 0% |
| | R202H | 60 → 70% | 70 → 100% | 100% |

Comparative Preparational Example 1

Preparation of Leuprolide-loaded RG502H Microspheres

Leuprolide was added to a RG502H polymer in an amount of 12 wt %, and glacial acetic acid was added to the mixture in an amount allowing a final polymer concentration of 5% (w/w), followed by homogeneous mixing. The resulting solution was supplied to a spray dryer at a flow rate of 2.4 ml/min, thus yielding leuprolide-loaded RG502H microspheres.

Comparative Preparational Example 2

Preparation of Leuprolide-loaded RG503H Microspheres

Leuprolide was added to a RG503H polymer in an amount of 12 wt %, and glacial acetic acid was added to the mixture in an amount allowing a final polymer concentration of 5% (w/w), followed by homogeneous mixing. The resulting solution was supplied to a spray dryer at a flow rate of 2.4 ml/min, thus yielding leuprolide-loaded RG503H microspheres.

Comparative Preparational Example 3

Preparation of Leuprolide-loaded R202H Microspheres

Leuprolide was added to a R202H polymer in an amount of 12 wt %, and glacial acetic acid was added to the mixture in an amount allowing a final polymer concentration of 5% (w/w), followed by homogeneous mixing. The resulting solution was supplied to a spray dryer at a flow rate of 2.4 ml/min, thus yielding leuprolide-loaded R202H microspheres.

Test Example 1

In Vitro Release Tests

In vitro release tests were carried out for the formulations 1, 2 and 3 prepared in Preparational Example 1 and the microspheres prepared in Comparative Preparational Examples 1, 2 and 3. The results are given in FIGS. 2a and 2b.

Figure 2A:
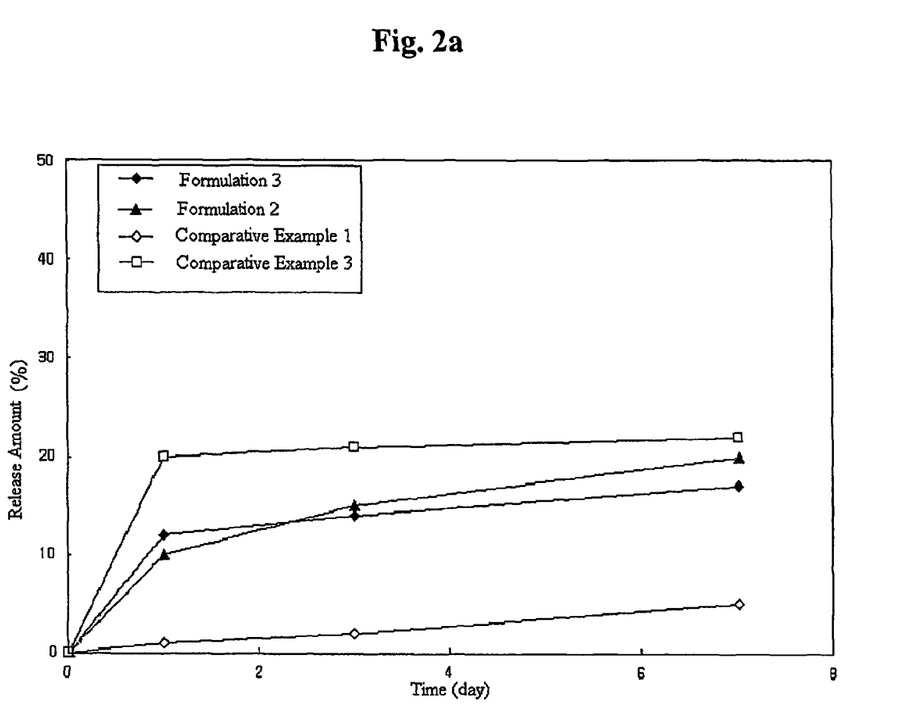
FIGS. 2a and 2b show results of in vitro release studies of microsphere blends with various polymer compositions, which are prepared according to a procedure of the Preparational Example 1.
Figure 2B:
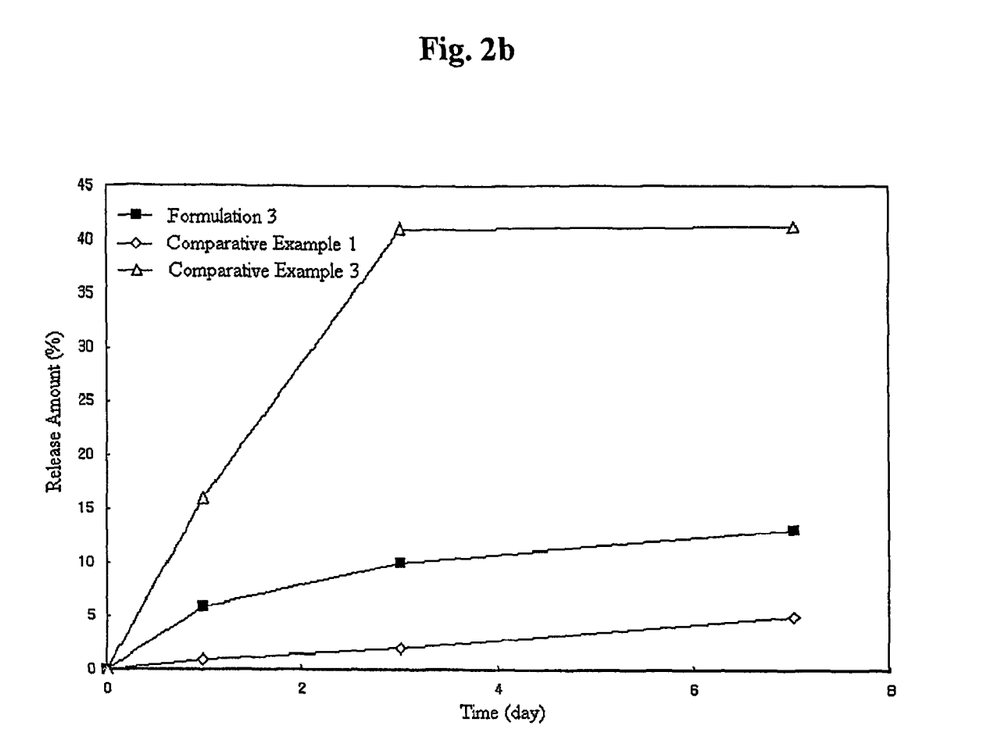

As shown in FIG. 2a, Formulation 1 which was prepared by a fixed single gradient at a 1:2 ratio of RG502H:RG03H showed a similar release profile that could be obtained by simply mixing the microspheres of Comparative Preparational Examples 1 (RG502H) and 2 (RG503H) at a ratio of 1:2. However, the release profile of Formulation 2, which was prepared using various different gradient programs according to the time, showed a lower initial release and a higher following release profile, which could not be obtained by mixing any ratios of the microspheres Comparative Preparational Examples 1 and 2. This result indicates that very delicate release profile can be adjusted by various mixed formulations prepared by this continuous process. FIG. 2b also showed that a mixed formulation prepared by this continuous process can reduce the initial release further while maintaining the following release profile even though more R202H polymers were used rather than RG502H polymers. However, if the microspheres of Comparative Preparational Examples 1 and 3 were simply mixed at a similar ratio, a high initial release would be shown.

Microspheres, prepared in the following Preparational Example and Comparative Preparational Examples by mixing solutions with different drug contents at proper ratios using a gradient pump and spray-drying the mixture, were found to effectively control an initial release and a continuous release of the drug.

Preparational Example 2

Preparation of a Mixed Formulation of Microspheres Containing Various Contents of Octreotide Octreotide was added to RG502H and RG504 polymers in amounts 5 wt % and 15 wt %, respectively, and glacial acetic acid was added to the mixture in an amount allowing a final polymer concentration of 5% (w/w), followed by homogeneous mixing. The resulting solutions were supplied to a spray dryer using a gradient pump at a total flow rate of 3 ml/min, and the mixture was spray-dried by controlling the mixing ratios of the fluids according to the time, thus yielding a mixed formulation of microspheres with various contents of octreotide. The ratios of the solutions according to the time are given in Table 2, below.

TABLE 2

| Solutions | Total flow rate (3 ml/min) | | | Final drug |
|---|---|---|---|---|
| (drug content %) | 0-3 min | 3-6 min | 6-9 min | content (%, w/w) |
| Formulation 4 RG502H(5%) RG504(15%) | 100 → 70% 0 → 30% | 70 → 60% 30 → 40% | 60% 40% | 7.3 |

Comparative Preparational Example 4

Preparation of RG502H Microspheres Containing a Low Content of Octreotide

Octreotide was added to a RG502H polymer in an amount of 5 wt %, and glacial acetic acid was added to the mixture in an amount allowing a final polymer concentration of 5% (w/w), followed by homogeneous mixing. The resulting solution was supplied to a spray dryer at a flow rate of 3 ml/min, thus yielding a formulation of RG502H microspheres containing 4.9% octreotide.

Comparative Preparational Example 5

Preparation of RG502H Microspheres Containing a High Content of Octreotide

Octreotide was added to a RG504 polymer in an amount of 15 wt %, and glacial acetic acid was added to the mixture in an amount allowing a final polymer concentration of 5% (w/w), followed by homogeneous mixing. The resulting solution was supplied to a spray dryer at a flow rate of 3 ml/min, thus yielding a formulation of RG504 microspheres containing 14.7% octreotide.

Test Example 2

In Vitro Release Tests

Figure 3:
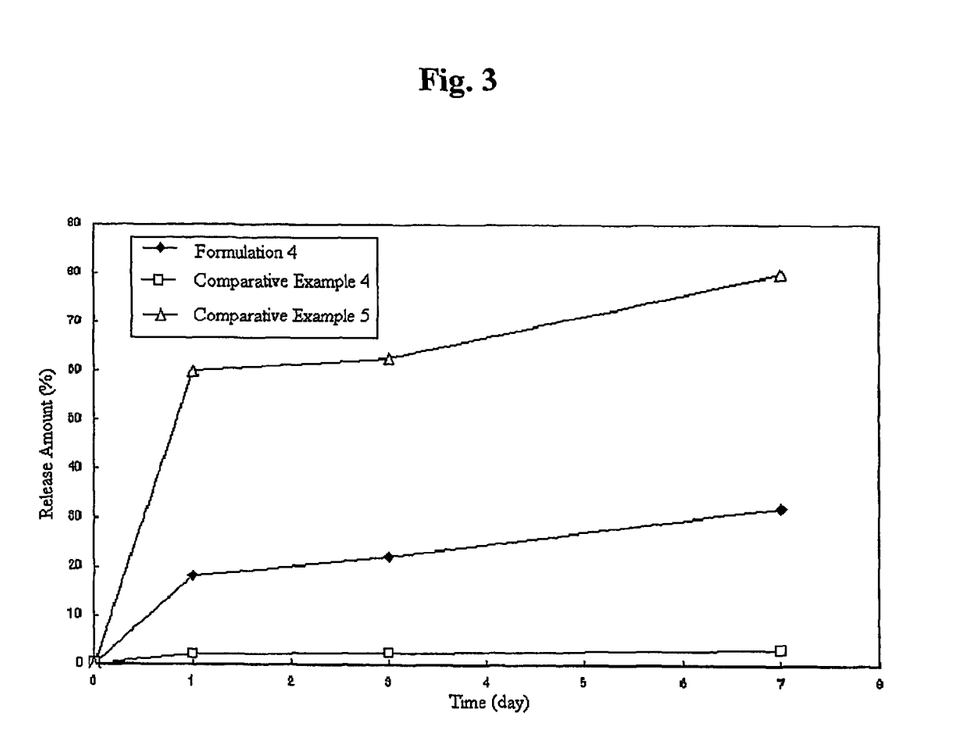
FIG. 3 shows results of in vitro release studies of a microsphere blend with various drug contents, which is prepared according to a procedure of the Preparational Example 2.

In vitro release tests were carried out for the formulation 4 prepared in Preparational Example 2 and the microspheres prepared in Comparative Preparational Examples 4 and 5. The results are given in FIG. 3.

Microspheres, prepared in the following Preparational Example and Comparative Preparational Examples by mixing solutions with different contents of an additive for drug release control at proper ratios using a gradient pump and spray-drying the mixture, were found to have various drug release patterns.

Preparational Example 3

Preparation of a Mixed Formulation of Triptorelin-loaded Microspheres Containing Various Contents of an Additive Triptorelin was added to a RG503H polymer in an amount of 2 wt %, and glacial acetic acid was added to the mixture in an amount allowing a final polymer concentration of 5% (w/w), followed by homogeneous mixing, thus yielding a solution. One more solution was prepared with the same composition to the first solution. One of the two identical solutions was added with 15 wt % of D-mannitol as an additive. Herein, since D-mannitol was not well dissolved in glacial acetic acid, it was added to the solution after being dissolved in double distilled water corresponding to 5 wt % of glacial acetic acid. The resulting solutions were supplied to a spray dryer using a gradient pump at a total flow rate of 3 ml/min, and the mixture was spray-dried by controlling the mixing ratios of the fluids according to the time, thus yielding a mixed formulation of triptorelin-loaded microspheres containing various additive contents. The ratios of the solutions according to the time are given in Table 3, below.

TABLE 3

| Solutions (additive content %) | Total flow rate (3 ml/min) | | |
|---|---|---|---|
| | 0-3 min | 3-6 min | 6-9 min |
| Formulation 5 RG503H(0%) RG503H(15%) | 100 → 70% 0 → 30% | 70 → 50% 30 → 50% | 50 → 40% 50 → 60% |

Comparative Preparational Example 6

Preparation of Triptorelin-loaded Microspheres not Containing an Additive

Triptorelin was added to a RG503H polymer in an amount of 2 wt %, and glacial acetic acid was added to the mixture in an amount allowing a final polymer concentration of 5% (w/w), followed by homogeneous mixing. The resulting solution was supplied to a spray dryer at a flow rate of 3 ml/min, thus yielding triptorelin-loaded RG503H microspheres.

Comparative Preparational Example 7

Preparation of Triptorelin-loaded Microspheres Containing an Additive

Triptorelin was added to a RG503H polymer in an amount of 2 wt %, and glacial acetic acid was added to the mixture in an amount allowing a final polymer concentration of 5% (w/w), followed by homogeneous mixing. The resulting solution was added with 15 wt % of D-mannitol as an additive. Herein, D-mannitol was added to the solution after being dissolved in double distilled water corresponding to 5 wt % of glacial acetic acid. The resulting solution was supplied to a spray dryer at a flow rate of 3 ml/min, thus yielding triptorelin-loaded RG503H microspheres containing D-mannitol.

Test Example 3

In Vitro Release Tests

Figure 4:
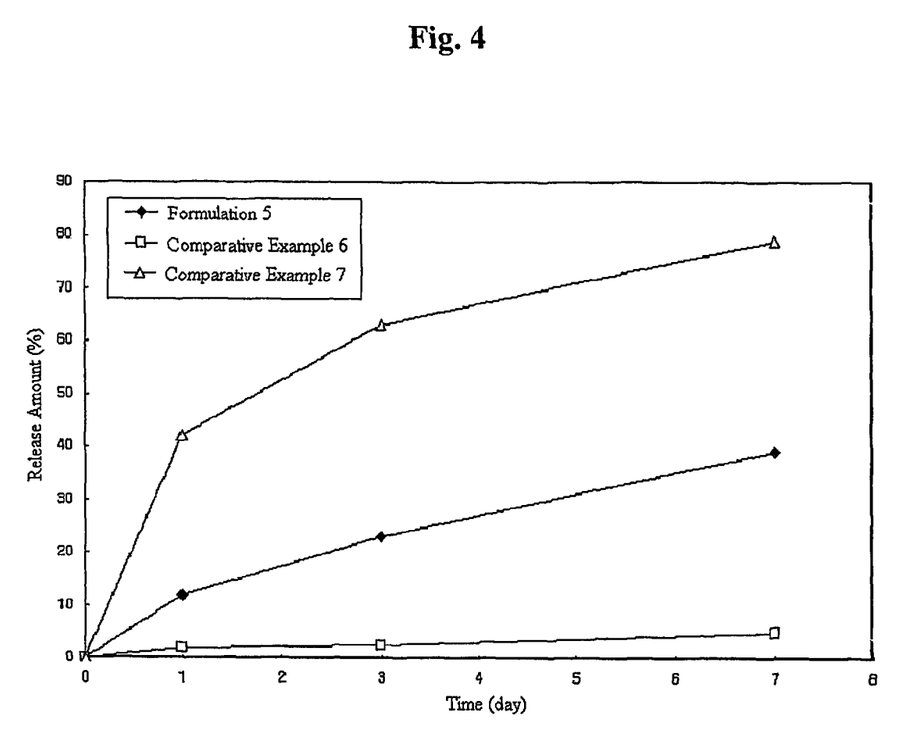
FIG. 4 shows results of in vitro release studies of a microsphere blend with various additive contents, which is prepared according to a procedure of the Preparational Example 3.

In vitro release tests were carried out for the formulation 5 prepared in Preparational Example 3 and the microspheres prepared in Comparative Preparational Examples 6 and 7. The results are given in FIG. 4.

The following Preparational Examples illustrate preparation of various microspheres using a gradient pump.

Preparational Example 4

Preparation of Goserelin-loaded Microspheres with Various Contents of Goserelin and Various Polymer To prepare microspheres with various contents of goserelin and polymers, solutions with different peptide contents and different polymer compositions were prepared. With four combinations, the solutions were supplied to a spray dryer at a total flow rate of 3 ml/min using a gradient pump, and spray-dried by controlling the mixing ratios of the fluids according to the time, thus yielding four mixed formulations of microspheres with different peptide contents and different polymer compositions. The compositions of the solutions and their ratios according to the time are given in Table 4, below. The peptide and the polymer were dissolved in glacial acetic acid, and a final polymer concentration was 5% (w/w).

TABLE 4

| | Solutions (drug content %) | Total flow rate (3 ml/min) | | |
|---|---|---|---|---|
| | | 0-3 min | 3-6 min | 6-9 min |
| Formulation 6 | RG504H(5%) | 0 → 20% | 20 → 50% | 50% |
| | RG502H(5%) | 100 → 80% | 80 → 50% | 50% |
| Formulation 7 | RG504H(5%) | 0 → 40% | 40 → 60% | 60 → 100% |
| | RG502H(10%) | 100 → 60% | 60 → 40% | 40 → 0% |
| Formulation 8 | RG502H(5%) | 100 → 90% | 90 → 70% | 70 → 50% |
| | RG502H(10%) | 0 → 10% | 10 → 30% | 30 → 50% |
| Formulation 9 | RG504H(5%) | 80% | 80 → 70% | 70 → 50% |
| | RG502H(10%) | 20% | 20 → 30% | 30 → 50% |

Preparational Example 5

Preparation of Microspheres with Various Contents of Bovine Serum Albumin

A mixed solution of bovine serum albumin and dextran sulfate at a weight ratio of 5:1 was spray-dried, thus generating first protein particles. As shown in Table 5a, below, the first protein particles were suspended in a polymer solution. The resulting solutions were supplied to a spray dryer at a total flow rate of 3 ml/min using a gradient pump, and spray-dried by controlling the mixing ratios of the fluids according to the time, thus yielding a mixed formulation of microspheres with various contents of bovine serum albumin. The ratios of the solutions according to the time are given in Table 5b, below.

TABLE 5a

| | Polymer (Conc. %, w/w, solvent:methylene chloride) | Conc. of protein particles (%, w/w) | Conc. of $ZnCl_2$ (%, w/w) |
|---|---|---|---|
| Solution A | RG502H(5%) | 10 | 1 |
| Solution B | RG504(5%) | 5 | 0 |

TABLE 5b

| | | Total flow rate (3 ml/min) | | |
|---|---|---|---|---|
| | | 0-3 min | 3-6 min | 6-9 min |
| Formulation 10 | Solution A | 95% | 95 → 80% | 80 → 50% |
| | Solution B | 5% | 5 → 20% | 20 → 50% |

Preparational Example 6

Preparation of Microspheres with Various Drug Contents by a Spray Freeze-drying Process Two solutions of 5 wt % RG504H polymer were prepared by dissolving the polymer in methylene chloride. Then, methanolic solutions of leuprolide were individually added to these polymer solutions resulting 2 wt % and 10 wt % of leuprolide solid content. The resulting two solutions were supplied to an ultrasonic nozzle (SONO-TEK Corporation) using a gradient pump at ratios as listed in Table 6, below, and sprayed on liquid nitrogen containing ethanol to directly freeze the sprayed solution. Liquid nitrogen was evaporated in a deep freezer. After methylene chloride came out into an ethanol layer, the frozen solution was dried, and the dried product was recovered.

TABLE 6

| | RG504H solution (Drug content %) | Total flow rate (3 ml/min) | | |
|---|---|---|---|---|
| | | 0-3 min | 3-6 min | 6-9 min |
| Formulation 11 | 2% | 0 → 40% | 40 → 60% | 60 → 100% |
| | 10% | 100 → 0% | 60 → 40% | 40 → 0% |
| Formulation 12 | 2% | 100 → 90% | 90 → 70% | 70 → 60% |
| | 10% | 0 → 10% | 10 → 30% | 30 → 40% |

As described hereinbefore, when sustained release microspheres are to be prepared with regard to polymer nature, drug-polymer affinity, most effective in vivo drug release patterns, and the like, sustained release microspheres with various compositions can be prepared by a continuous one-step process by spray-drying using a gradient pump, not by a complex process of separately preparing several formulations and mixing them. In addition, the present method is effective in achieving a finely controlled drug release, which cannot be accomplished by simple combinations of microspheres, by preparing a microsphere formulation with various compositions. Therefore, the present method facilitates selection and preparation of microsphere formulations with the most suitable drug release kinetics for treatment of diseases.

Although a preferred embodiment of the present invention has been described for illustrative purposes, those skilled in the art will appreciate that various modifications, additions and substitutions are possible, without departing from the scope and spirit of the present invention as disclosed in the accompanying claims.

What is claimed is:

1. A method of preparing a mixed formulation of sustained release microspheres by a continuous one-step process, comprising:
    preparing two to four different fluids for preparation of the sustained release microspheres containing a biodegradable polymer and a peptide drug; and
    continuously supplying the mixed fluids from the two to four different fluids to a dryer via a single spray nozzle by controlling the mixing ratios of the fluids according to the time to dry the fluids.

2. The method as set forth in claim 1, wherein the fluids contains the biodegradable polymer, the peptide drug, an additive and a solvent with different compositions of one or more of the components.

3. The method as set forth in claim 1, wherein the sprayed fluids are dried by a spray-drying method, a spray freeze-drying method, or a supercritical fluid-based drying method.

4. The method as set forth in claim 1, further comprising dispersing the sustained release microspheres in a solution containing a dispersion excipient and freeze-drying a resulting solution.

5. The method as set forth in claim 1, wherein the peptide drug is selected from among peptides of 2 to 60 amino acid residues in length and salts thereof.

6. The method as set forth in claim 5, wherein the peptide drug is selected from among luteinizing hormone releasing hormone (LHRH) analogs, octreotide and salts thereof.

7. The method as set forth in claim 6, wherein the LHRH analogs are selected from among triptorelin, leuprolide, goserelin, nafarelin, buserelin, histerelin and salts thereof.

8. The method as set forth in claim 1, wherein the biodegradable polymer is selected from polylactide, polyglycolide, poly(lactide-co-glycolide), polyorthoesters, polyanhydrides, polyamino acids, polyhydroxybutyric acid, polycaprolactone, polyalkylcarbonate, lipids, fatty acids, waxes, and derivatives and mixtures thereof.

9. The method as set forth in claim 8, wherein the biodegradable polymer is selected from polylactide and poly(lactide-co-glycolide).

* * * * *